United States Patent
Shinohara et al.

(10) Patent No.: US 11,490,846 B2
(45) Date of Patent: Nov. 8, 2022

(54) BIOELECTRODE AND METHOD FOR PRODUCING BIOELECTRODE

(71) Applicant: TATSUTA ELECTRIC WIRE & CABLE CO., LTD., Osaka (JP)

(72) Inventors: Keisho Shinohara, Kyoto (JP); Takashi Morita, Kyoto (JP); Shinji Yoshino, Kyoto (JP); Tsunehiko Terada, Kyoto (JP); Akio Takahashi, Kyoto (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 994 days.

(21) Appl. No.: 16/311,334

(22) PCT Filed: Jun. 23, 2017

(86) PCT No.: PCT/JP2017/023226
§ 371 (c)(1),
(2) Date: Dec. 19, 2018

(87) PCT Pub. No.: WO2018/003697
PCT Pub. Date: Jan. 4, 2018

(65) Prior Publication Data
US 2019/0320923 A1    Oct. 24, 2019

(30) Foreign Application Priority Data
Jun. 30, 2016    (JP) .............................. JP2016-130503

(51) Int. Cl.
*A61B 5/25*    (2021.01)
*B32B 1/08*    (2006.01)
(Continued)

(52) U.S. Cl.
CPC ................ *A61B 5/25* (2021.01); *A61B 5/291* (2021.01); *B32B 1/08* (2013.01); *C09J 9/02* (2013.01);
(Continued)

(58) Field of Classification Search
CPC ..... A61B 5/25; A61B 2562/0215; B32B 5/16; B32B 2255/205; B32B 2255/26
See application file for complete search history.

(56) References Cited

U.S. PATENT DOCUMENTS

| 4,270,543 A | * | 6/1981 | Tabuchi | ................... A61B 5/25 600/391 |
| 4,377,170 A | | 3/1983 | Carim | |

(Continued)

FOREIGN PATENT DOCUMENTS

| CN | 1132530 A | 10/1996 |
| CN | 1143312 A | 2/1997 |

(Continued)

OTHER PUBLICATIONS

Office Action dated Oct. 15, 2019 issued for co-pending U.S. Appl. No. 16/309,729.
(Continued)

*Primary Examiner* — Eun Hwa Kim
(74) *Attorney, Agent, or Firm* — Rankin, Hill & Clark LLP (57) ABSTRACT

A bioelectrode (1) includes: a main electrode film (3); a nonpolarizable electrode film (4) disposed on one surface of the main electrode film (3); and a conductive gel film (5) disposed on the opposite surface of the nonpolarizable electrode film (4) from the main electrode film. The nonpolarizable electrode film (4) is constituted by an electrode (Continued)

film that contains supported silver chloride, the supported silver chloride including (i) a support and (ii) silver chloride supported on the support.

12 Claims, 6 Drawing Sheets

(51) Int. Cl.
  *C09J 9/02* (2006.01)
  *A61B 5/291* (2021.01)
(52) U.S. Cl.
  CPC . *A61B 2562/0215* (2017.08); *A61B 2562/125* (2013.01)

(56) References Cited

U.S. PATENT DOCUMENTS

| | | | |
|---|---|---|---|
| 4,852,571 A * | 8/1989 | Gadsby | A61B 5/274 600/397 |
| 5,505,200 A | 4/1996 | Takaki | |
| 5,565,143 A | 10/1996 | Chan | |
| 5,851,438 A | 12/1998 | Chan | |
| 2001/0031988 A1 | 10/2001 | Kurata | |
| 2003/0051799 A1 | 3/2003 | Stevenson | |
| 2003/0088239 A1 * | 5/2003 | Takaki | A61N 1/0496 606/1 |
| 2008/0177166 A1 | 7/2008 | Pronovost et al. | |
| 2008/0311476 A1 | 12/2008 | Katai et al. | |
| 2009/0303660 A1 | 12/2009 | Nair et al. | |
| 2010/0185071 A1 | 7/2010 | Simpson et al. | |
| 2012/0034385 A1 | 2/2012 | Chen et al. | |
| 2012/0034391 A1 | 2/2012 | Chang et al. | |
| 2014/0081118 A1 | 3/2014 | Reinhold, Jr. | |
| 2014/0212667 A1 | 7/2014 | Iwanaga et al. | |
| 2016/0137848 A1 | 5/2016 | Iwanaga et al. | |
| 2018/0215941 A1 | 8/2018 | Hagar | |

FOREIGN PATENT DOCUMENTS

| | | | |
|---|---|---|---|
| CN | 1459474 A | 12/2003 | |
| CN | 1531650 A | 9/2004 | |
| CN | 1544323 A | 11/2004 | |
| CN | 2685874 Y | 3/2005 | |
| CN | 1664020 A | 9/2005 | |
| CN | 1821182 A | 8/2006 | |
| CN | 101037220 A | 9/2007 | |
| CN | 101081699 A | 12/2007 | |
| CN | 101148347 A | 3/2008 | |
| CN | 101276903 A | 10/2008 | |
| CN | 101420032 A | 4/2009 | |
| CN | 101435792 A | 5/2009 | |
| CN | 102091331 A | 6/2011 | |
| CN | 102160135 A | 8/2011 | |
| CN | 102198929 A | 9/2011 | |
| CN | 102285659 A | 12/2011 | |
| CN | 102380334 A | 3/2012 | |
| CN | 102525449 A | 7/2012 | |
| CN | 102976457 A | 3/2013 | |
| CN | 103149258 A | 6/2013 | |
| CN | 103180920 A | 6/2013 | |
| CN | 103192070 A | 7/2013 | |
| CN | 103403121 A | 11/2013 | |
| CN | 103783081 A | 5/2014 | |
| CN | 103798289 A | 5/2014 | |
| CN | 103861657 A | 6/2014 | |
| CN | 103965658 A | 8/2014 | |
| CN | 204306820 U | 5/2015 | |
| CN | 105334250 A | 2/2016 | |
| CN | 105581793 A | 5/2016 | |
| EP | 0698129 | 2/1996 | |
| EP | 2000173 A2 | 12/2008 | |
| JP | 51026789 A | 3/1976 | |
| JP | 53-19870 A | 2/1978 | |
| JP | 57021302 U1 | 2/1982 | |
| JP | 58007227 A | 1/1983 | |
| JP | 59190649 A | 10/1984 | |
| JP | S6410164 A | 1/1989 | |
| JP | H05095922 A | 4/1993 | |
| JP | 05176904 A | 7/1993 | |
| JP | 05182513 A | 7/1993 | |
| JP | 3149597 B2 | 3/2001 | |
| JP | 2001292972 A | 10/2001 | |
| JP | 2003-133267 A | 5/2003 | |
| JP | 2007085763 A | 4/2007 | |
| JP | 2012-91358 A | 5/2012 | |
| JP | 2014517759 A | 7/2014 | |
| JP | 2015210883 A | 11/2015 | |
| JP | 2018168445 A | 11/2018 | |
| WO | 2001004614 A1 | 1/2001 | |
| WO | 2007111368 A1 | 10/2007 | |
| WO | 2010/020007 A1 | 2/2010 | |
| WO | 2014/129597 A1 | 8/2014 | |
| WO | 2015162931 A1 | 10/2015 | |

OTHER PUBLICATIONS

Chinese Office Action (CNOA) dated Jun. 17, 2021 for Chinese Patent Application No. 201780038250.6 and its English translation.
Min et al., "Development of white antibacterial pigment based on silver chloride nanoparticles and mesoporous silica and its polymer composite", Elsevier, 2009, Microporous and mesoporous materials 128, pp. 19-25; Cited in U.S. Office Action.
U.S. Office Action dated Jun. 24, 2020 issued in the related U.S. Appl. No. 16/311,444.
Chinese Office Action (CNOA) dated Sep. 3, 2021 for Chinese Patent Application No. 201780038347.7 and its English translation.
Chinese Office Action (CNOA) dated Jun. 25, 2021 issued in the corresponding Chinese Patent Application No. 201780038347.7 and its English translation.
Office Action dated Apr. 15, 2019 filed in co-pending U.S. Appl. No. 16/309,729.
Luo, "Preparation of a New Type of Inorganic Antibacterial and Evaluation of Its Antibacterial Activity", China Excellent Master's Thesis Full Text Database; 2003, English abstract included for pp. 4-5; Cited in CNOA dated Mar. 3, 2021.
Chinese Office Action (CNOA) dated Mar. 3, 2021 issued in the corresponding Chinese Patent Application No. 201780038612.1; Partial English translation.
Chinese Office Action (CNOA) dated Mar. 22, 2021 issued in the corresponding Chinese Patent Application No. 201780038347.7; Partial English translation.
Chinese Office Action (CNOA) dated Mar. 25, 2021 issued in the corresponding Chinese Patent Application No. 201780038250.6; Partial English translation.
International Search Report dated Sep. 12, 2017 filed in PCT/JP2017/023234.
International Preliminary Report on Patentability dated Jan. 10, 2019 filed in PCT/JP2017/023234.
T. Endo et al. "Preparation and Catalytic Activities of Noble Metal Binary Particle Dendrimer Nanocomposites", Journal of the Japan Society of Colour Material, 2005, pp. 185-190, vol. 78, No. 4, Japan Society of Colour Material, Japan; Partial translation.
International Search Report dated Aug. 8, 2017 filed in PCT/JP2017/023228.
International Preliminary Report on Patentability dated Jan. 10, 2019 filed in PCT/JP2017/023228.
International Preliminary Report on Patentability dated Jan. 10, 2019 filed in PCT/JP2017/023226.
International Search Report dated Sep. 26, 2017 filed in PCT/JP2017/023226.
Chinese Office Action (CNOA) dated Jul. 27, 2021 issued in corresponding Chinese Patent Application No. 201780038612.1 and its English translation.
Leng, "Preparation of Silver-doped Mesoporous Silica Coating and Characterization of Its Antimicrobial Activity", China Master's Theses Full-text Database, Sep. 15, 2012, total 45 pages, English abstract; Cited in CNOA.

(56) References Cited

OTHER PUBLICATIONS

Luo, "The Preparation of Silver-loaded Nano Silica Coating and the Characterization of Its Antimicrobial Activity and Biosafety", China Master's Theses Full-text Database, Aug. 15, 2013, total 48 pages, English abstract; Cited in CNOA.

Xu et al., "SiO2@Ag/AgCl: a low-cost and highly efficient plasmonic photocatalyst for degrading rhodamine B under visible light irradiation", RSC Advances, 2014, vol. 4, pp. 64747-64755; Cited in CNOA.

Chinese Office Action (CNOA) dated Sep. 8, 2021 for Chinese Patent Application No. 201780038250.6 and its English translation.

Tuncer, "Effects of Chloride Ion and the Types of Oxides on the Antibacterial Activities of Norganic Oxide Supported Ag Materials", Izmir Institute of Technology, Jul. 2007; Cited in US Office Action.

U.S. Office Action dated Jan. 10, 2020 issued in the related U.S. Appl. No. 16/311,444.

Japanese Office Action (JPOA) dated Jun. 9, 2020 issued in the corresponding Japanese Patent Application No. 2018-525134 and its English translation.

\* cited by examiner

BIOELECTRODE AND METHOD FOR PRODUCING BIOELECTRODE

TECHNICAL FIELD

The present invention relates to a bioelectrode and a method of forming a bioelectrode.

BACKGROUND ART

Patent Literature 1 discloses a bioelectrode including a nonpolarizable electrode film that contains silver/silver chloride.

CITATION LIST

Patent Literature

[Patent Literature 1]
Japanese Patent Application Publication, Tokukaihei, No. 5-95922
[Patent Literature 2]
Japanese Patent Application Publication, Tokukai, No. 2015-210883
[Patent Literature 3]
PCT International Publication No. WO2015/162931

SUMMARY OF INVENTION

Technical Problem

The bioelectrode of Patent Literature 1 includes a nonpolarizable electrode film containing silver/silver chloride. Silver, which is contained in the nonpolarizable electrode film, is expensive, and thus the bioelectrode of the Patent Literature 1 has an issue in that it is costly.

An object of the present invention is to provide a bioelectrode that is less expensive but maintains its nonpolarizing properties.

Solution to Problem

In order to attain the above object, a subject matter in accordance with Aspect 1 of the present invention is a bioelectrode that includes: a main electrode film; a nonpolarizable electrode film disposed on one surface of the main electrode film; and a conductive gel film disposed on an opposite surface of the nonpolarizable electrode film from the main electrode film, the nonpolarizable electrode film being constituted by an electrode film that contains supported silver chloride, the supported silver chloride including (i) a support and (ii) silver chloride supported on the support.

According to the above arrangement, the nonpolarizable electrode film is constituted by an electrode film that contains supported silver chloride, which includes (i) a support and (ii) silver chloride supported on the support. This makes it possible to reduce the total amount of silver as compared to the nonpolarizable electrode film containing silver/silver chloride disclosed in Patent Literature 1, when both are to achieve the same total area of exposure of silver chloride within the nonpolarizable electrode film. This makes it possible to obtain a bioelectrode that is less expensive but maintains its nonpolarizing properties.

DESCRIPTION OF EMBODIMENTS

The following description will discuss embodiments of the present invention with reference to the accompanying drawings.

[1] Embodiment 1

Figure 1:
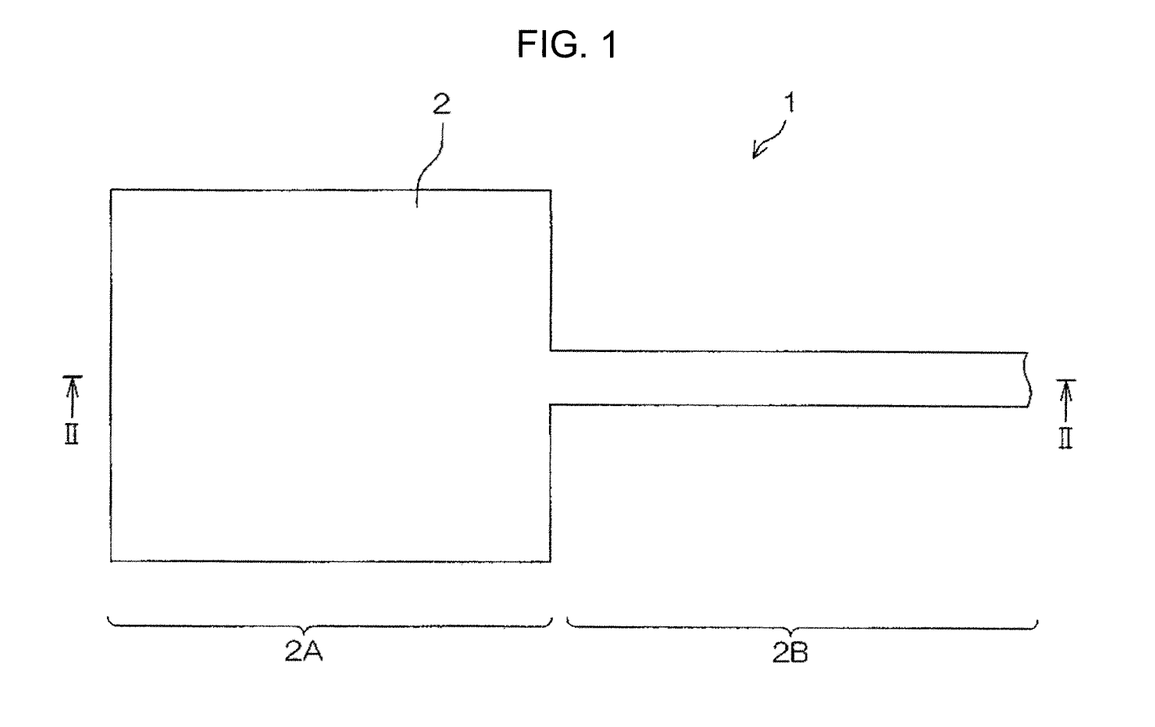
FIG. 1 is a plan view schematically illustrating a bioelectrode in accordance with Embodiment 1 of the present invention
Figure 2:
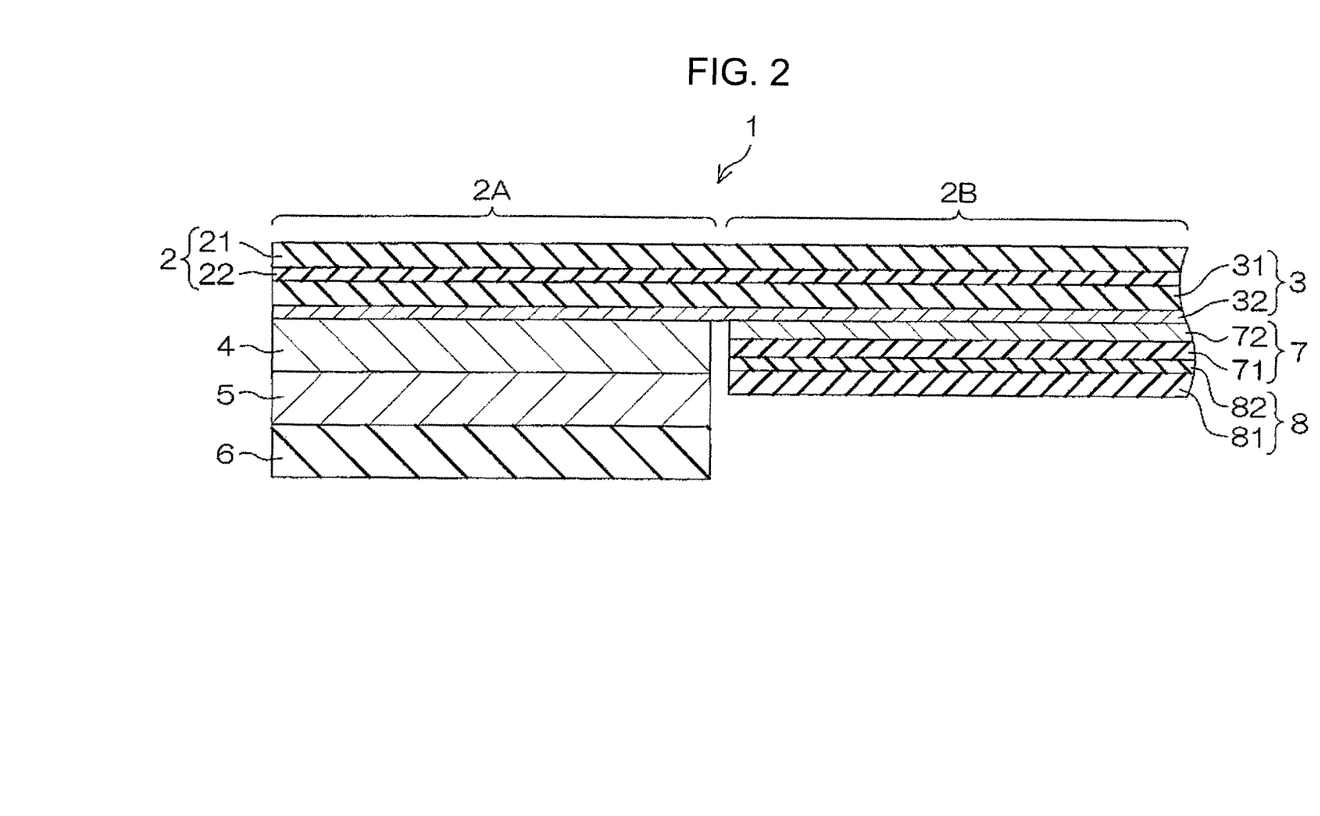
FIG. 2 is a schematic cross-sectional view taken along line II-II in FIG. 1.

FIG. 1 is a plan view schematically illustrating a bioelectrode in accordance with Embodiment 1 of the present invention. FIG. 2 is a schematic cross-sectional view taken along line II-II in FIG. 1.

A bioelectrode 1 includes a protective film 2, a main electrode film 3, a nonpolarizable electrode film 4, a conductive gel film 5, a release film 6, a lead wire 7, and a lead wire protective film 8.

The protective film 2 includes: an electrode protective portion 2A rectangular in shape in plan view; and a lead wire protective portion 2B that extends from the middle of an edge (in FIG. 1, the edge on the right-hand side) of the electrode protective portion 2A in one direction (in FIG. 1, to the right). In Embodiment 1, the protective film 2 is constituted by: a nonwoven cloth 21; and a resin film 22 disposed on one surface (in FIG. 2, on the bottom surface) of the nonwoven cloth 81. In Embodiment 1, the resin film 22 is made of polyethylene (PE).

The main electrode film 3 is substantially equal in shape to the protective film 2 in plan view. In Embodiment 1, the main electrode film 3 is constituted by: a base 31; and a metal film 32 disposed on one surface (in FIG. 2, on the bottom surface) of the base 31. In Embodiment 1, the base 31 is made of polyethylene terephthalate (PET), and the metal film 32 is constituted by an evaporated silver film. Such an evaporated silver film can be formed by evaporating silver on the one surface of the base 31. The main electrode film 3 is joined to one surface (in FIG. 2, the bottom surface) of the protective film 2 such that the base 31's surface (in FIG. 2, the top surface) of the main electrode film 3 faces the one surface of the protective film 2.

The nonpolarizable electrode film 4 is disposed on the opposite surface of the main electrode film 3 from the protective film 2 (i.e., on the metal film 32's surface of the main electrode film 3) so as to reside in a region corresponding to the electrode protective portion 2A of the protective film 2. The nonpolarizable electrode film 4 is constituted by an electrode film that contains supported silver chloride, which includes: a support; and silver chloride supported on the support. Such an electrode film (nonpolarizable electrode film 4) can be made from a silver chloride paste containing supported silver chloride. The silver chloride paste containing supported silver chloride will be described later in detail.

The conductive gel film 5 is disposed on the opposite surface of the nonpolarizable electrode film 4 from the main electrode film 3 such that that surface of the nonpolarizable electrode film 4 is substantially entirely covered by the conductive gel film 5. The conductive gel film 5 is a part that makes direct contact with the skin of a living body during use of the bioelectrode 1. The conductive gel film 5 may be, for example, hydrogel HIT-B3R, CR-H, or CR-RA available from SEKISUI CHEMICAL CO., LTD., or the like.

The release film 6 is disposed on the opposite surface of the nonpolarizable electrode film 4 from the main electrode film 3 such that that surface of the nonpolarizable electrode film 4 is substantially entirely covered by the release film 6. The release film 6 may be, for example, release paper (separate paper), a fluorine film, a polyethylene naphthalate (PEN) film coated on one surface or both surfaces with a silicone-based or silicone-free release agent (e.g., melamine-based release agent, acrylic release agent, or the like), a polyethylene terephthalate (PET) film, or the like. The release film 6 is removed when the bioelectrode 1 is used.

The lead wire 7 is constituted by: a base 71 that is in the form of a strip and that is smaller in width than the lead wire protective portion 2B of the protective film 2 in plan view: and a metal film 72 that is disposed on one surface (in FIG. 2, on the top surface) of the base 71. In Embodiment 1, the base 71 is made of PET, and the metal film 72 is constituted by an evaporated silver film. Such an evaporated silver film can be formed by evaporating silver on the one surface of the base 71. The lead wire 7 is joined to the opposite surface of the main electrode film 3 from the protective film 2 (i.e., to the metal film 32's surface of the main electrode film 3, or the bottom surface of the main electrode film 3 in FIG. 2) so as to reside in a region corresponding to the lead wire protective portion 2B of the protective film 2 such that the metal film 72's surface of the lead wire 7 faces that surface of the main electrode film 3. The electrode protective portion 2A-side end of the lead wire 7 is short of the electrode protective portion 2A, and is not in contact with the nonpolarizable electrode film 4, in plan view.

The lead wire protective film 8 is substantially equal in shape to the lead wire protective portion 2B of the protective film 2 in plan view. In Embodiment 1, the lead wire protective film 8 is constituted by: a nonwoven cloth 81; and a resin film 82 disposed on one surface (in FIG. 2, the top surface) of the nonwoven cloth 81. In Embodiment 1, the resin film 82 is made of PE. The lead wire protective film 8 is joined to the opposite surface of the main electrode film 3 from the protective film 2 (i.e., the metal film 32's surface of the main electrode film 3, or the bottom surface of the main electrode film 3 in FIG. 2) so as to reside in the region corresponding to the lead wire protective portion 2B of the protective film 2 such that the resin film 82' surface of the lead wire protective film 8 faces that surface of the main electrode film 3 and such that the lead wire protective film 8 covers the lead wire 7. In this way, the lead wire 7 is covered by: the protective film 2 mainly covering the top surface of the lead wire 7; and the lead wire protective film 8 mainly covering the bottom surface of the lead wire.

The bioelectrode 1 is produced in the following manner, for example.

A long rectangular protective film precursor (a member that will be formed into the protective film 2) that is long in one direction in plan view and that is equal in width to the foregoing electrode protective portion 2A is prepared. A long rectangular lead wire protective film precursor (a member that will be formed into the lead wire protective film 8) that is long in one direction in plan view and that is substantially equal in width to the protective film precursor is prepared.

A rectangular main electrode film precursor (a member that will be formed into the main electrode film 3) that is long in one direction in plan view and that is substantially equal in width to the electrode protective portion 2A is prepared. Then, a multilayer electrode film is prepared, in which the nonpolarizable electrode film 4 is disposed at one end (a region corresponding to the electrode protective portion 2A of the protective film 2) of one surface (the metal film's surface, or the bottom surface in FIG. 2) of the main electrode film precursor. The multilayer electrode film is produced by, for example, forming a silver chloride paste, which contains supported silver chloride, on the one end of the one surface (the metal film's surface) of the main electrode film precursor, and then drying the solvent contained in the silver chloride paste. The formation of the silver chloride paste on the main electrode film precursor may be carried out by printing, transferring, application, or the like. The drying of the solvent is carried out by, for example, a heat treatment at 110° C. for 3 min. to 5 min. The thickness of the nonpolarizable electrode film 4 is, for example, any thickness falling within the range of from 1 µm to 100 µm, and is, for example, 20 µm.

Next, a release-film-attached gel sheet, which is constituted by: the release film 6; and the conductive gel film 5 disposed on one surface (in FIG. 2, the top surface) of the release film 6, is prepared. The lead wire 7 is also prepared.

Then, the multilayer electrode film is first joined to one surface (in FIG. 2, the bottom surface) of the protective film precursor such that the main electrode film precursor's surface faces the one surface of the protective film precursor. Next, the release-film-attached gel sheet is joined to the nonpolarizable electrode film 4's surface of the multilayer electrode film such that the conductive gel film 5's surface of the release-film-attached gel sheet faces the nonpolarizable electrode film 4's surface of the multilayer electrode film.

Next, the lead wire 7 is joined to the opposite surface of the main electrode film precursor from the protective film precursor so as to reside in a region corresponding to a portion, of the protective film precursor, which will become the lead wire protective portion such that the metal film 72's surface (in FIG. 2, the top surface) of the lead wire 7 faces that surface of the main electrode film precursor.

Next, the lead wire protective film precursor is joined to the same surface of the main electrode film precursor as where the lead wire is joined (in FIG. 2, the bottom surface of the main electrode film precursor) so as to reside in the region corresponding to the portion, of the protective film precursor, which will become the lead wire protective portion such that the resin film 82's surface of the lead wire protective film precursor faces that surface of the main electrode film precursor and such that the lead wire protective film precursor covers the lead wire 7.

Lastly, the protective film precursor, the main electrode film precursor, and the lead wire protective film precursor are patterned into the shapes of the protective film 2, the main electrode film 3, and the lead wire protective film 8, respectively. In this way, the bioelectrode 1 illustrated in FIGS. 1 and 2 is obtained.

In Embodiment 1, the nonpolarizable electrode film 4 is constituted by an electrode film containing supported silver chloride, which includes: a support; and silver chloride supported on the support. This makes it possible to reduce the total amount of silver as compared to the nonpolarizable electrode film containing silver/silver chloride disclosed in Patent Literature 1, when both are to achieve the same total area of exposure of silver chloride within the nonpolarizable electrode film 4. This makes it possible to obtain a bioelectrode that is less expensive but maintains its nonpolarizing properties.

In Embodiment 1, the main electrode film 3 is constituted by: the base 31; and the metal film 32 disposed on one surface (in FIG. 2, the bottom surface) of the base 31; however, the main electrode film 3 may be composed only of a metal film such as a silver film. In Embodiment 1, the metal film 32 is constituted by an evaporated silver film; however, the metal film 32 may be an evaporated film of some other metal other than silver. The metal film 32 may be a sputtered metal film formed by sputtering or a metal plating film formed by plating.

[2] Embodiment 2

Figure 3:
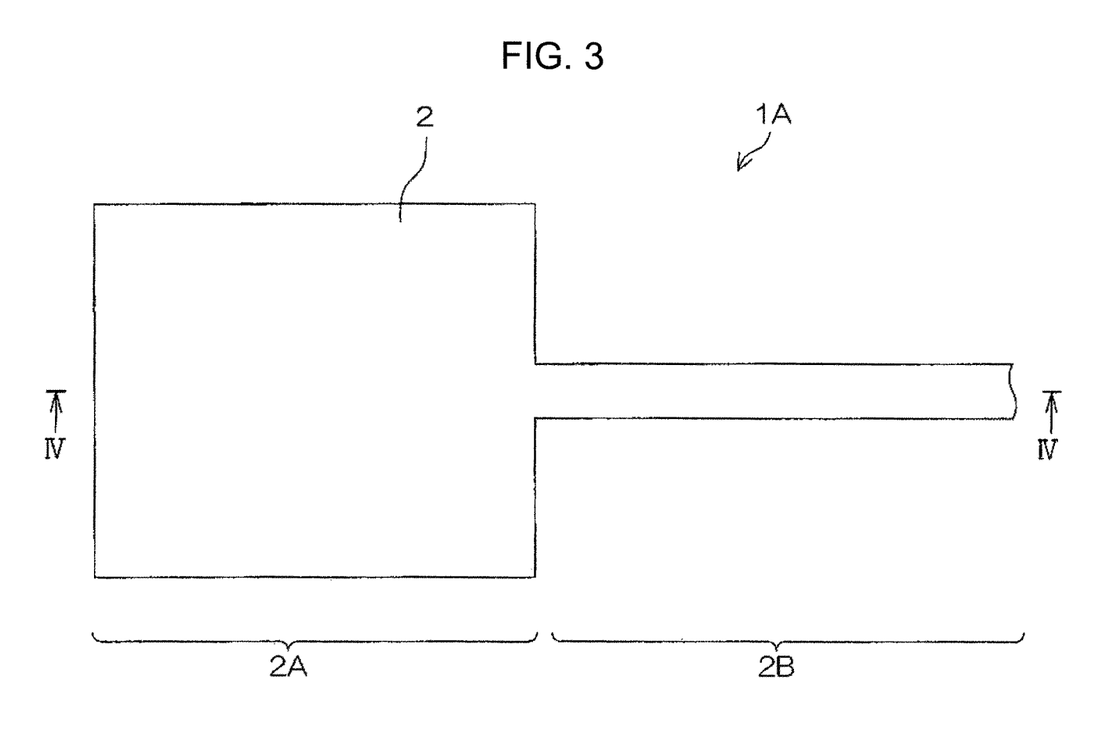
FIG. 3 is a plan view schematically illustrating a bioelectrode in accordance with Embodiment 2 of the present invention
Figure 4:
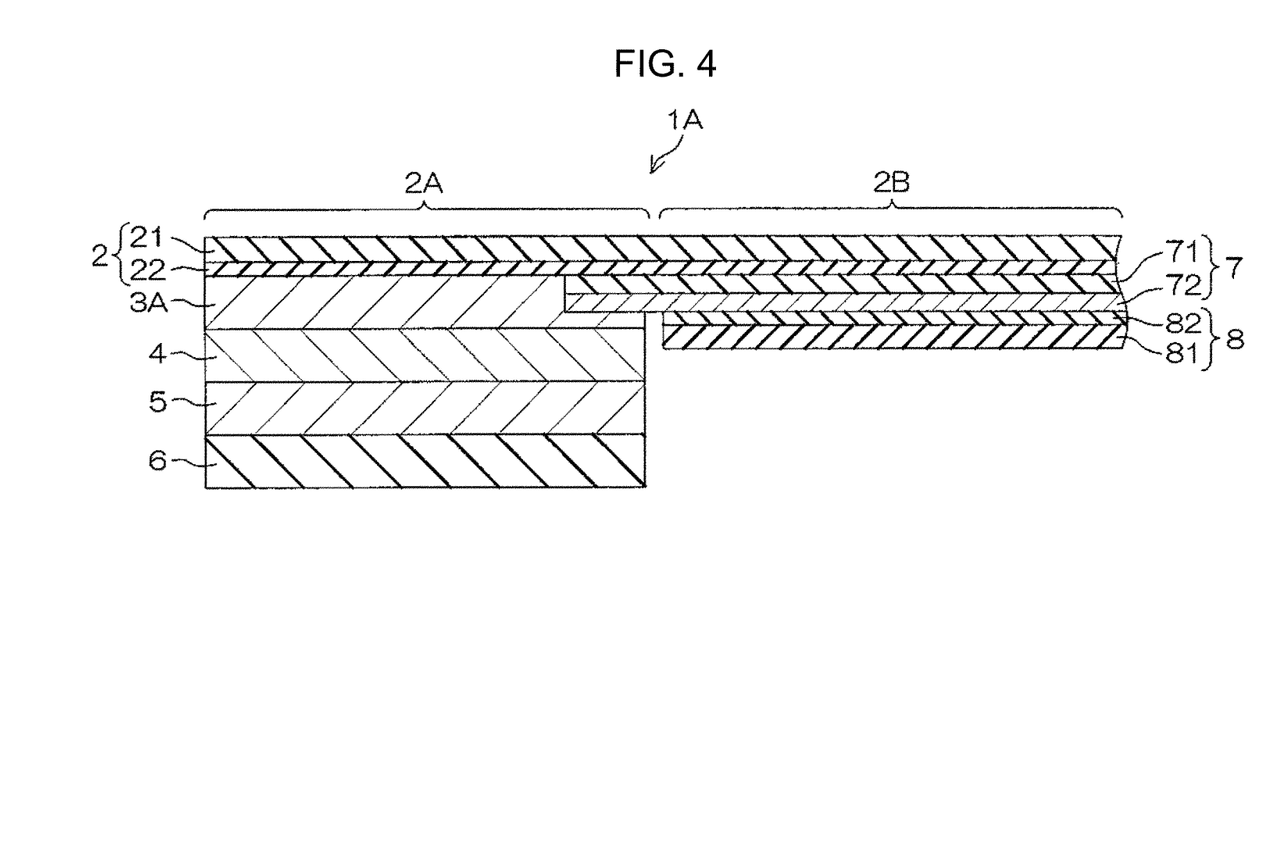
FIG. 4 is a schematic cross-sectional view taken along line IV-IV in FIG. 3.

FIG. 3 is a plan view schematically illustrating a bioelectrode in accordance with Embodiment 2 of the present invention. FIG. 4 is a schematic cross-sectional view taken along line IV-IV in FIG. 3.

In FIGS. 3 and 4, parts corresponding to the respective parts of the foregoing FIGS. 1 and 2 are assigned identical reference numerals.

As with the bioelectrode 1 in accordance with the foregoing Embodiment 1, a bioelectrode 1A in accordance with Embodiment 2 includes a protective film 2, a main electrode film 3A, a nonpolarizable electrode film 4, a conductive gel film 5, a release film 6, a lead wire 7, and a lead wire protective film 8. The protective film 2, the nonpolarizable electrode film 4, the conductive gel film 5, the release film 6, the lead wire 7, and the lead wire protective film 8 of the bioelectrode 1A in accordance with Embodiment 2 are equal in shape and arrangement to the protective film 2, the nonpolarizable electrode film 4, the conductive gel film 5, the release film 6, the lead wire 7, and the lead wire protective film 8 in accordance with Embodiment 1, respectively.

The bioelectrode 1A in accordance with Embodiment 2 is different from the bioelectrode 1 in accordance with the foregoing Embodiment 1 in terms of attachment structure of the lead wire 7 and the shape and material of the main electrode film 3A.

The main electrode film 3A is equal in shape to the electrode protective portion 2A of the protective film 2 in plan view. The main electrode film 3 in Embodiment 2 is constituted by a silver-containing electrode film. Such an electrode film can be formed from, for example, a silver paste (silver ink). The lead wire 7 is joined to the resin film 22's surface (in FIG. 4, the bottom surface) of the protective film 2 such that the base 71's surface of the lead wire 7 faces the resin film 22's surface of the protective film 2. The lead wire 7 is disposed such that, when viewed in plan view, most of the lead wire 7 extends along the widthwise centerline of the resin film 22's surface of the lead wire protective portion 2B of the protective film 2, whereas the electrode protective portion 2A-side end of the lead wire 7 protrudes from the lead wire protective portion 2B of the protective film 2 to reach the electrode protective portion 2A.

The nonpolarizable electrode film 4 is disposed so as to substantially entirely cover the opposite surface of the main electrode film 3A from the protective film 2 (in FIG. 4, the bottom surface of the main electrode film 3A) and cover one end of the lead wire 7.

The conductive gel film 5 is disposed so as to substantially entirely cover the opposite surface of the nonpolarizable electrode film 4 from the main electrode film 3A. The release film 6 is disposed so as to substantially entirely cover the opposite surface of the nonpolarizable electrode film 4 from the main electrode film 3A. The lead wire protective film 8 is joined to the same surface of the protective film 2 as where the lead wire 7 is disposed (in FIG. 4, the bottom surface of the protective film 2) such that the resin film 82's surface of the lead wire protective film 8 faces that surface of the protective film 2 and such that the lead wire protective film 8 covers the lead wire 7. In this way, the lead wire 7 is covered by: the protective film 2 mainly covering the top surface of the lead wire 7; and the lead wire protective film 8 mainly covering the bottom surface of the lead wire.

The bioelectrode 1A is produced in the following manner, for example.

A long rectangular protective film precursor (a member that will be formed into the protective film 2) that is long in one direction in plan view and that is equal in width to the foregoing electrode protective portion 2A is prepared. A long rectangular lead wire protective film precursor (a member that will be formed into the lead wire protective film 8) that is long in one direction in plan view and that is equal in width to the protective film precursor is prepared.

A multilayer-electrode-film-supporting film, which is constituted by: a polyester (PET) film base (not illustrated); and a multilayer film (multilayer electrode film) made up of the main electrode film 3A and the nonpolarizable electrode film 4 and disposed on the polyester (PET) film base, is prepared. The multilayer-electrode-film-supporting film is produced in the following manner, for example. Specifically, first, a silver paste is formed on a release film (not illustrated), and then the silver paste is dried, and thereby the main electrode film 3A is formed on the polyester film base. Then, a silver chloride paste containing supported silver chloride is formed on a surface of the main electrode film 3A, and then the silver chloride paste is dried, and thereby the nonpolarizable electrode film 4 is formed on the main electrode film 3A. In this way, the multilayer-electrode-film-supporting film is obtained. The thickness of the nonpolarizable electrode film 4 is any thickness falling within the range of, for example, from 1 μm to 100 μm, and is, for example, 20 μm.

A release-film-attached gel sheet, which is constituted by: the release film 6; and the conductive gel film 5 disposed on one surface (in FIG. 4, the top surface) of the release film 6, is prepared. The lead wire 7 is also prepared.

Then, the lead wire 7 is first joined to one surface (in FIG. 4, the bottom surface) of the protective film precursor such that the base 71's surface of the lead wire 7 faces the one surface of the protective film precursor. Here, the lead wire 7 is disposed such that most of the lead wire 7 extends along the widthwise centerline of the resin film 22's surface of the lead wire protective portion 2B of the protective film 2 and that the electrode protective portion 2A-side end of the lead wire 7 protrudes from the lead wire protective portion 2B to reach the electrode protective portion 2A.

Next, the polyester film base is removed from the multilayer-electrode-film-supporting film, and thereby the multilayer electrode film made up of the main electrode film 3A and the nonpolarizable electrode film 4 is obtained. Then, the multilayer electrode film is joined to one surface (in FIG. 4, the bottom surface) of the protective film precursor so as to reside in a region corresponding to the electrode protective portion 2A such that the main electrode film 3A's surface of the multilayer electrode film faces the one surface of the protective film precursor and such that the multilayer electrode film covers one end of the lead wire 7. Next, the release-film-attached gel sheet is joined to the nonpolarizable electrode film 4's surface of the multilayer electrode film such that the conductive gel film 5's surface of the release-film-attached gel sheet faces the nonpolarizable electrode film 4's surface of the multilayer electrode film.

Next, the lead wire protective film precursor is joined to the same surface of the protective film precursor as where the lead wire 7 is joined (in FIG. 4, the bottom surface of the protective film precursor) so as to reside in a region corresponding to a portion, of the protective film precursor, which will become the lead wire protective portion such that the resin film 82's surface of the lead wire protective film precursor faces that surface of the protective film precursor and such that the lead wire protective film precursor covers the lead wire 7.

Lastly, the protective film precursor and the lead wire protective film precursor are patterned into the shapes of the protective film 2 and the lead wire protective film 8, respectively. In this way, the bioelectrode 1A illustrated in FIGS. 3 and 4 is obtained.

Also in Embodiment 2, the nonpolarizable electrode film 4 is constituted by an electrode film containing supported silver chloride, which includes: a support; and silver chloride supported on the support. This makes it possible to reduce the total amount of silver as compared to the nonpolarizable electrode film containing silver/silver chloride disclosed in Patent Literature 1, when both are to achieve the same total area of exposure of silver chloride within the nonpolarizable electrode film 4. This makes it possible to obtain a bioelectrode that is less expensive but maintains its nonpolarizing properties.

In Embodiment 2, the main electrode film 3 is constituted by a silver-containing electrode film; however, the main electrode film 3 may be constituted by a carbon-containing electrode film. Such an electrode film may be formed from a carbon paste. Alternatively, the main electrode film 3 may be formed from some other conductive paste other than the silver paste and the carbon paste.

[3] Silver Chloride Paste for Use in Formation of Nonpolarizable Electrode Film

The silver chloride paste for use in formation of the nonpolarizable electrode film 4 in this embodiment contains (i) a binder resin and (ii) supported silver chloride including: a support; and silver chloride supported on the support. Such a silver chloride paste contains supported silver chloride, and thus has nonpolarizing properties.

[3.1] Binder Resin

The binder resin is, for example, a thermoplastic resin. Specific examples of the binder resin include polyester resins, polyurethane resins, acrylic resins, alkyd resins, phenoxy resins, butyral resins, and polyvinylalcohol resins. Examples of polyester resins include: solvent-soluble-type polyesters TP-220, TP-217, TP-249, TP-235, TP-236, TP-290, TP-270, LP-035, LP-033, LP-050, LP-011, LP-022, and TP-219 available from The Nippon Synthetic Chemical Industry Co., Ltd.; elitel resins UE3220, UE3223, UE3230, UE3231, UE3400, UE3500, UE3200, UE9200, UE3201, UE3203, UE3600, UE9600, UE3660, UE3690, UE3210, UE3215, UE3216, UE3620, UE3240, and UE3250 available from UNITIKA LTD.; and ARON MELT PES3 10S30 and PES360HVXM30 available from TOAGOSEI CO., LTD.

[3.2] Supported Silver Chloride

The supported silver chloride includes: a support; and silver chloride supported on the support.

[3.2.1] Support

A material for the support can be any of various materials such as metals (preferably other than silver), nonmetals, organic substances, and inorganic substances. In order for the supported silver chloride to be readily dispersed in the binder resin, it is preferable to prevent the supported silver chloride from precipitating in the binder resin. To achieve this, the support is preferably one that is equal or close in density to the binder resin. Furthermore, the support is preferably a low-cost support on which silver chloride can be easily supported.

Specifically, the support can be (1) an acrylic resin, a polyurethane resin, a polyester resin, or a polyamide resin; (2) polymer particles composed of an epoxy resin or the like, silica beads, mica beads, or glass beads, or (3) inorganic particles composed of calcium carbonate or the like.

[3.2.2] Example 1 of Supported Silver Chloride

Example 1 of the supported silver chloride is silica-supported silver chloride, which is constituted by: silica (silicon dioxide): and silver chloride supported on the silica.

The silica which supports silver chloride may be wet-process silica such as precipitated silica or gelation method silica (gel method silica), or may be dry-process silica. The silica is preferably gelation method silica. In this embodiment, the silica is gelation method silica.

Figure 5:
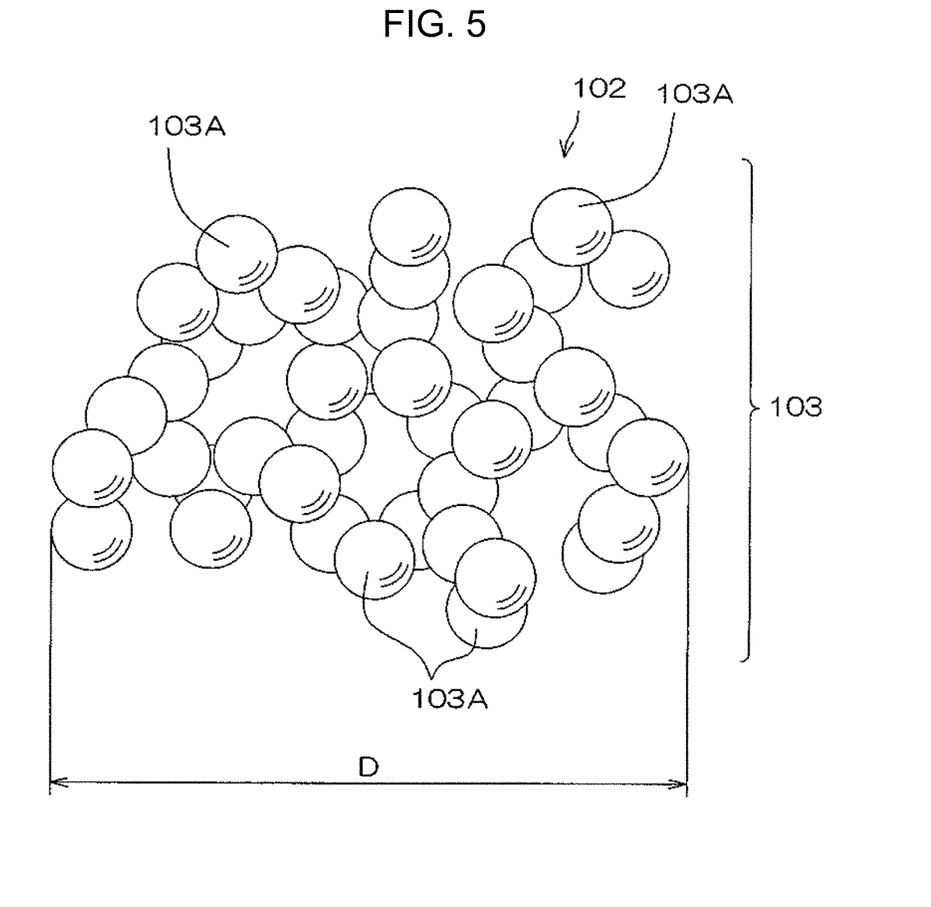
FIG. 5 schematically illustrates one example of a particulate structure of silica constituted by gelation method silica.

FIG. 5 schematically illustrates one example of a particulate structure of silica constituted by gelation method silica. Silica 102, which is constituted by gelation method silica, has a particulate structure such that, for example, a plurality of primary particles (skeleton grains) 103A are grouped in the form of a bunch of grapes to form a secondary particle 103.

In the following descriptions, the specific surface area of silica refers to surface area per unit mass. The surface area of silica is the sum of the external surface area and the internal surface area (i.e., the surface area of the walls of pores in the silica) of silica. The pore volume of silica refers to the volume of pores in silica per unit mass. The mean pore size of silica refers to the mean of the diameters of the pores (cavities) in silica. The mean particle size of silica refers to the mean of diameters D (see FIG. 5) of secondary particles.

The specific surface area of the silica is preferably not less than 20 $m^2/g$ and not more than 1000 $m^2/g$, particularly preferably not less than 100 $m^2/g$ and not more than 700 $m^2/g$. The pore volume of the silica is preferably not less than 0.2 ml/g and not more than 2.0 ml/g, particularly preferably not less than 0.3 ml/g and not more than 1.2 ml/g. The mean pore size of the silica is preferably not less than 2 nm and not greater than 100 nm, particularly preferably not less than 2 nm and not greater than 30 nm. The mean particle size of the silica is preferably not less than 1 μm and not greater than 50 μm, particularly preferably not less than 2 μm and not greater than 30 μm.

Figure 6:
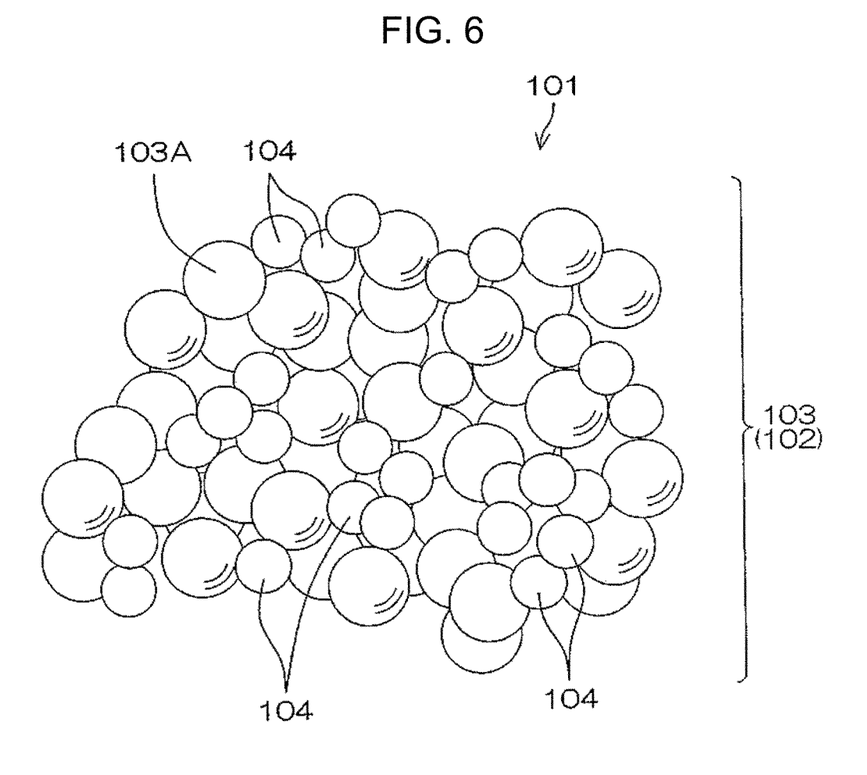
FIG. 6 schematically illustrates one example of a particulate structure of silica-supported silver chloride which is constituted by: silica constituted by gelation method silica; and silver chloride supported on the silica.
Figure 7:
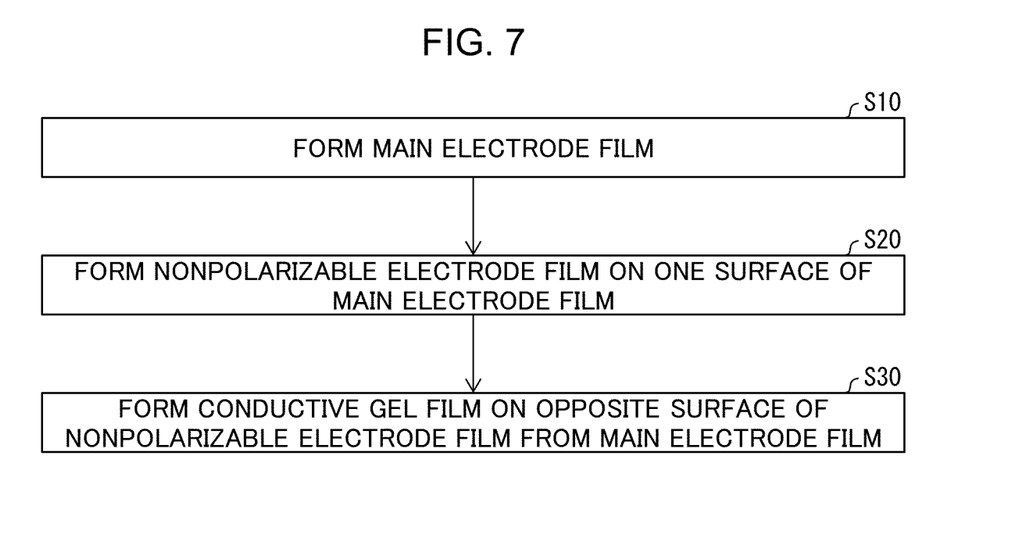
FIG. 7 is a flowchart illustrating a method of forming a bioelectrode.

FIG. 6 schematically illustrates one example of a particulate structure of silica-supported silver chloride which is constituted by: silica constituted by gelation method silica;

and silver chloride supported on the silica. Silica-supported silver chloride 101 illustrated in FIG. 6 includes: the silica 102; and silver chloride 104 supported on the surface (including the walls of pores) of the silica 102.

The silica-supported silver chloride is produced by, for example, a production method discussed below. The production method includes the steps of: producing a silver compound solution by dissolving a silver compound in a solvent; and allowing the silver compound to be supported on the silica (including the walls of pores) with the use of the silver compound solution. The silver compound used here is silver nitrate, silver chloride, or the like.

For example, in a case where the silver compound is silver nitrate, a silver nitrate solution is first produced by dissolving silver nitrate powder in an aqueous solvent. Next, the silver nitrate solution is used to allow silver nitrate to be supported on silica. A method used to allow silver nitrate to be supported on silica is, for example, precipitation, gelatinization, impregnation, ion exchange, or the like method. Then, the silver nitrate supported on silica is allowed to react with a chloride-ion-containing compound such as hydrochloric acid or sodium chloride, and thereby silver chloride is supported on the silica.

For example, in a case where the silver compound is silver chloride, a silver chloride solution is first produced by dissolving silver chloride powder in an aqueous solution such as ammonia water, a concentrated hydrochloric acid solution, an aqueous alkaline cyanide solution, an aqueous thiosulfate solution, or an aqueous ammonium carbonate solution. Next, the silver chloride solution is used to allow silver chloride to be supported on silica. A method used to allow silver chloride to be supported on silica is, for example, precipitation, gelatinization, impregnation, ion exchange, or the like method. Then, an organic solvent that dissolves in an aqueous solvent, such as methanol, ethanol, isopropyl alcohol, methyl cellosolve, or butyl cellosolve, is added to the silver chloride supported on silica, and thereby the silver chloride is supported on silica.

[3.2.2.1] Example 1 of Silica-Supported Silver Chloride

Example 1 of silica-supported silver chloride includes: silica which is constituted by gelation method silica (SYLYSIA710 (trade name) available from FUJI SILYSIA CHEMICAL LTD.); and silver chloride (AgCl) supported on the silica. The silica (silicon dioxide) content of the silica-supported silver chloride of Example 1 is 61 wt %, and the silver chloride content of the silica-supported silver chloride is 39 wt %. In Example 1, the specific surface area of the silica is 397 $m^2/g$, and the mean particle size of the silica is 2.9 μm.

The following description discusses a method of producing Example 1 of silica-supported silver chloride. First, 40 g of silver nitrate powder was dissolved in 50 ml of ion-exchanged water to prepare a silver nitrate solution. Next, 20 g of silica (SYLYSIA710 (trade name) available from FUJI SILYSIA CHEMICAL LTD.) was added to the silver nitrate solution and stirred for 4 hours. Next, a solid component was collected from the stirred solution with the use of type 5A filter paper, and the collected solid component was dried in a shelf-type dryer at 120° C. for 16 hours. In this way, silica-supported silver nitrate, which is constituted by: silica; and silver nitrate supported on the silica, was obtained.

Next, about 34 g of the silica-supported silver nitrate was added to 200 ml of 1M hydrochloric acid, and stirred for 4 hours. Next, a solid component was collected from the stirred solution with the use of type 5A filter paper, and the collected solid component was washed with 200 ml of ion-exchanged water. Next, the washed solid component was dried in a shelf-type dryer at 120° C. for 16 hours, and then was pulverized. In this way, about 30 g of silica supporting silver chloride (silica-supported silver chloride) was obtained.

[3.2.3] Another Method of Producing Supported Silver Chloride

The supported silver chloride can alternatively be produced by coating silver on a support and then carrying out chlorination. A method of coating silver on a support can be the method disclosed in Patent Literatures 2 and 3 and the like.

[3.3] Example of Method of Producing Silver Chloride Paste

The following description discusses an example of a method of producing a silver chloride paste in a case where the supported silver chloride is silica-supported silver chloride.

In a vessel with a lid, 50 g powder of silica-supported silver chloride was placed. In the silica-supported silver chloride, the amount of silver chloride supported on silica is any amount falling within the range of 0.1 wt % to 80 wt %.

Next, 25 g of a solvent mixture of methyl ethyl ketone (MEK), ethyl acetate, and toluene (mix ratio: 1:1:1) was added to the vessel, where the solvent was mixed with the powder of silica-supported silver chloride.

Then, 50 g of a binder resin (solvent-soluble-type polyester LP-035 (solid content: 40%) available from The Nippon Synthetic Chemical Industry Co., Ltd.) was added to the vessel and stirred. Specifically, with the use of a stirrer (TK Homodisper MODEL2.5 available from PRIMIX Corporation), stirring was carried out at 3500 r/min for 10 minutes. In this way, a fluidic silver chloride paste with no powder agglomerations was obtained.

Note that the binder resin may be changed from the solvent-soluble-type polyester LP-035 (solid content: 40%) available from The Nippon Synthetic Chemical Industry Co., Ltd. to, for example, elite1 No. 3220 (solid content: 40%) available from UNITIKA LTD., elite1 No. 9200 (solid content: 40%) available from UNITIKA LTD., or the like.

The stirrer may be some other kind of stirrer, such as a propeller stirrer.

[3.4] Advantages of Silver Chloride Paste Containing Silica-Supported Silver Chloride The silver chloride paste containing silica-supported silver chloride is advantageous in the following aspects.

Silver chloride agglomerates easily (has low dispersibility), whereas silica does not easily agglomerate (has high dispersibility). Therefore, silica-supported silver chloride is more dispersible and less likely to agglomerate than silver chloride. Because of this, according to the silver chloride paste containing silica-supported silver chloride, silver chloride (silica-supported silver chloride) is less likely to agglomerate.

The silica-supported silver chloride is such that silver chloride is supported on silica (including the walls of pores). This makes it possible to increase the surface area of silver chloride as compared to the conventional silver/silver chloride paste, when the silver chloride paste containing silica-supported silver chloride and the conventional silver/silver chloride paste are equal in the total amount of silver chloride in the paste. This makes it possible to enhance polarization-reducing effect.

The silica-supported silver chloride is such that silver chloride is supported on silica (including the walls of pores). This makes it possible to reduce the amount of silver chloride (or silver) as compared to the conventional silver/silver chloride paste, when the silver chloride paste containing silica-supported silver chloride and the conventional silver/silver chloride paste are to achieve the same total area of exposure of silver chloride within the paste. This makes it possible to provide a less expensive silver chloride paste.

According to the silver chloride paste containing silica-supported silver chloride, silver chloride supported on the walls of pores (cavities) in the silica does not receive much light. Therefore, the silver chloride paste containing silica-supported silver chloride has improved light resistance as compared to the conventional silver/silver chloride paste which contains silver particles and fine silver chloride particles.

[Recap]

A bioelectrode in accordance with Aspect 2 of the present invention is arranged such that, in Aspect 1, the main electrode film includes (i) a base and (ii) a metal film disposed on one surface of the base.

A bioelectrode in accordance with Aspect 3 of the present invention is arranged such that, in Aspect 1, the main electrode film is composed of a metal film.

A bioelectrode in accordance with Aspect 4 of the present invention is arranged such that, in Aspect 2 or 3, the metal film is one selected from evaporated metal films, sputtered metal films, and metal plating films.

A bioelectrode in accordance with Aspect 5 of the present invention is arranged such that, in any of Aspects 2 to 4, the metal film is composed of silver.

A bioelectrode in accordance with Aspect 6 of the present invention is arranged such that, in Aspect 1, the main electrode film is constituted by a silver-containing electrode film or a carbon-containing electrode film.

A bioelectrode in accordance with Aspect 7 of the present invention further includes, in any of Aspects 1 to 6, a protective film disposed on an opposite surface of the main electrode film from the nonpolarizable electrode film.

A bioelectrode in accordance with Aspect 8 further includes, in any of Aspects 1 to 7, a release film disposed on an opposite surface of the conductive gel film from the nonpolarizable electrode film.

A bioelectrode in accordance with Aspect 9 of the present invention is arranged such that, in any of Aspects 1 to 8, the support is silica.

A bioelectrode in accordance with Aspect 10 further includes, in any of Aspects 1 to 9, a lead wire having one end thereof electrically connected to the main electrode film.

A bioelectrode in accordance with Aspect 11 of the present invention includes a main electrode film, a nonpolarizable electrode film, and a conductive gel film arranged in this order, the nonpolarizable electrode film being constituted by an electrode film that contains supported silver chloride, the supported silver chloride including (i) a support and (ii) silver chloride supported on the support.

A method of forming a bioelectrode in accordance with Aspect 12 of the present invention includes the steps of: (S10) forming a main electrode film; (S20) forming a nonpolarizable electrode film on one surface of the main electrode film; and (S30) forming a conductive gel film on an opposite surface of the nonpolarizable electrode film from the main electrode film, the nonpolarizable electrode film being constituted by an electrode film that contains supported silver chloride, the supported silver chloride including (i) a support and (ii) silver chloride supported on the support.

A method of forming a bioelectrode in accordance with Aspect 13 of the present invention includes the steps of: (S10) forming a main electrode film; (S20) forming a conductive gel film on one surface of the main electrode film; and (S30) forming a nonpolarizable electrode film on an opposite surface of the conductive gel film from the main electrode film, the nonpolarizable electrode film being constituted by an electrode film that contains supported silver chloride, the supported silver chloride including (i) a support and (ii) silver chloride supported on the support.

The present invention can be modified in various manners within the matters described in claims. Furthermore, the present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1 Bioelectrode
2 Protective film
2A Electrode protective portion
2B Lead wire protective portion
21 Nonwoven cloth
22 Resin film
3, 3A Main electrode film
31 Base
32 Metal film
4 Nonpolarizable electrode film
5 Conductive gel film
6 Release film
7 Lead wire
71 Base
72 Metal film
8 Lead wire protective film
81 Nonwoven cloth
82 Resin film

The invention claimed is:

1. A bioelectrode comprising:
a main electrode film;
a nonpolarizable electrode film disposed on one surface of the main electrode film; and
a conductive gel film disposed on an opposite surface of the nonpolarizable electrode film from the main electrode film,
the nonpolarizable electrode film being constituted by an electrode film that contains supported silver chloride, the supported silver chloride including (i) a support and (ii) silver chloride supported on the support,
wherein the support is silica,
the silver chloride is supported on a region including walls of pores in the silica, and
the main electrode film includes (i) a base and (ii) a metal film disposed on one surface of the base.

2. The bioelectrode according to claim 1, wherein the main electrode film is composed of a metal film.

3. The bioelectrode according to claim 2, wherein the metal film is one selected from evaporated metal films, sputtered metal films, and metal plating films.

4. The bioelectrode according to claim 2, wherein the metal film is composed of silver.

5. The bioelectrode according to claim 1, wherein the main electrode film is constituted by a silver-containing electrode film or a carbon-containing electrode film.

6. The bioelectrode according to claim 1, further comprising a protective film disposed on an opposite surface of the main electrode film from the nonpolarizable electrode film.

7. The bioelectrode according to claim 1, further comprising a release film disposed on an opposite surface of the conductive gel film from the nonpolarizable electrode film.

8. The bioelectrode according to claim 1, further comprising a lead wire having one end thereof electrically connected to the main electrode film.

9. The bioelectrode according to claim 1, wherein a specific surface area of the silica is not less than 20 $m^2/g$ and not more than 1000 $m^2/g$, and a pore volume of the silica is not less than 0.2 ml/g and not more than 2.0 ml/g.

10. A method of forming a bioelectrode, comprising the steps of:
    forming a main electrode film;
    forming a nonpolarizable electrode film on one surface of the main electrode film; and
    forming a conductive gel film on an opposite surface of the nonpolarizable electrode film from the main electrode film,
    the nonpolarizable electrode film being constituted by an electrode film that contains supported silver chloride, the supported silver chloride including (i) a support and (ii) silver chloride supported on the support,
    wherein the support is silica,
    the silver chloride is supported on a region including walls of pores in the silica; and
    the main electrode film includes (i) a base and (ii) a metal film disposed on one surface of the base.

11. The method according to claim 10, wherein a specific surface area of the silica is not less than 20 $m^2/g$ and not more than 1000 $m^2/g$, and a pore volume of the silica is not less than 0.2 ml/g and not more than 2.0 ml/g.

12. A bioelectrode comprising:
    a main electrode film;
    a nonpolarizable electrode film disposed on one surface of the main electrode film; and
    a conductive gel film disposed on an opposite surface of the nonpolarizable electrode film from the main electrode film, the nonpolarizable electrode film being constituted by an electrode film that contains supported silver chloride, the supported silver chloride including (i) a support and (ii) silver chloride supported on the support,
    wherein the support is silica,
    the silver chloride is supported on a region including walls of pores in the silica, and
    the main electrode film is composed of a metal film.

* * * * *